US009911166B2

(12) United States Patent
Reid et al.

(10) Patent No.: US 9,911,166 B2
(45) Date of Patent: Mar. 6, 2018

(54) SYSTEMS AND METHODS FOR THREE-DIMENSIONAL INTERACTION MONITORING IN AN EMS ENVIRONMENT

(71) Applicant: ZOLL MEDICAL CORPORATION, Chelmsford, MA (US)

(72) Inventors: C. Shane Reid, Denver, CO (US); Chad Ashmore, Frederick, CO (US); Robert H. Gotschall, Thornton, CO (US); Martin Bures, Somerville, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 25 days.

(21) Appl. No.: 14/040,147

(22) Filed: Sep. 27, 2013

(65) Prior Publication Data
US 2014/0096091 A1    Apr. 3, 2014

Related U.S. Application Data

(60) Provisional application No. 61/707,671, filed on Sep. 28, 2012, provisional application No. 61/707,665, filed on Sep. 28, 2012.

(51) Int. Cl.
*G06F 3/01* (2006.01)
*G06Q 50/22* (2018.01)
(Continued)

(52) U.S. Cl.
CPC ............ *G06Q 50/22* (2013.01); *G06F 3/017* (2013.01); *G06F 19/3462* (2013.01); *G06Q 10/00* (2013.01); *G06T 7/20* (2013.01)

(58) Field of Classification Search
CPC ....................................................... G06F 3/01
See application file for complete search history.

(56) References Cited

U.S. PATENT DOCUMENTS 5,534,917 A    7/1996 MacDougall
5,850,352 A    12/1998 Moezzi et al.
(Continued)

FOREIGN PATENT DOCUMENTS

JP    2003-24386      1/2003
JP    2005-40613 A    2/2005
(Continued)

OTHER PUBLICATIONS

International Search Report and Written Opinion issued in PCT/US2013/062261, dated May 27, 2014, 11 pages.
(Continued)

*Primary Examiner* — David Choi
(74) *Attorney, Agent, or Firm* — Wilmer Cutler Pickering Hale and Dorr LLP

(57) ABSTRACT

A method for tracking interactions in an emergency response environment according to embodiments of the present invention includes receiving color images and depth information from within a field of view of a sensor array; maintaining an emergency encounter record; monitoring one or both of a position of an object and movement of the object in the emergency response environment based on the color images and depth information received by the sensor array; and recording an occurrence of a condition in the emergency encounter record, wherein the condition is based on the one or both of the position of the object and the movement of the object.

24 Claims, 9 Drawing Sheets

(51) Int. Cl.
*G06T 7/20* (2017.01)
*G06F 19/00* (2018.01)
*G06Q 10/00* (2012.01)

(56) References Cited

U.S. PATENT DOCUMENTS

| | | | |
|---|---|---|---|
| 6,115,052 A | 9/2000 | Freeman et al. | |
| 6,236,737 B1 | 5/2001 | Gregson et al. | |
| 6,347,299 B1* | 2/2002 | Holzman | G06F 3/16 704/270 |
| 6,610,010 B2* | 8/2003 | Sjoqvist | A61B 5/742 128/903 |
| 6,741,977 B1 | 5/2004 | Nagaya et al. | |
| 6,968,294 B2 | 11/2005 | Gutta et al. | |
| 6,984,208 B2 | 1/2006 | Zheng | |
| 7,058,204 B2 | 6/2006 | Hildreth et al. | |
| 7,095,401 B2 | 8/2006 | Liu et al. | |
| 7,110,569 B2 | 9/2006 | Brodsky et al. | |
| 7,143,044 B2 | 11/2006 | Zadrozny et al. | |
| 7,212,109 B2 | 5/2007 | Morita et al. | |
| 7,225,131 B1 | 5/2007 | Bangalore et al. | |
| 7,227,526 B2 | 6/2007 | Hildreth et al. | |
| 7,274,290 B2 | 9/2007 | Morita et al. | |
| 7,333,090 B2 | 2/2008 | Tanaka et al. | |
| 7,340,077 B2* | 3/2008 | Gokturk | G06F 3/017 348/208.14 |
| 7,379,563 B2 | 5/2008 | Shamaie | |
| 7,379,566 B2 | 5/2008 | Hildreth | |
| 7,382,895 B2 | 6/2008 | Bramblet et al. | |
| 7,389,591 B2 | 6/2008 | Jaiswal et al. | |
| 7,421,093 B2 | 9/2008 | Hildreth et al. | |
| 7,421,647 B2 | 9/2008 | Reiner | |
| 7,430,312 B2 | 9/2008 | Gu | |
| 7,499,862 B1 | 3/2009 | Bangalore et al. | |
| 7,501,995 B2 | 3/2009 | Morita et al. | |
| 7,539,532 B2 | 5/2009 | Tran | |
| 7,607,079 B2 | 10/2009 | Reiner | |
| 7,643,862 B2 | 1/2010 | Schoenefeld | |
| 7,668,340 B2 | 2/2010 | Cohen et al. | |
| 7,694,240 B2 | 4/2010 | Kariathungal et al. | |
| 7,698,002 B2 | 4/2010 | Music et al. | |
| 7,813,784 B2 | 10/2010 | Marquart et al. | |
| 7,818,177 B1 | 10/2010 | Bangalore et al. | |
| 7,945,076 B2 | 5/2011 | DeLean | |
| 7,961,910 B2 | 6/2011 | Lee et al. | |
| 7,987,069 B2 | 7/2011 | Rodgers et al. | |
| 7,996,793 B2 | 8/2011 | Latta et al. | |
| 8,009,867 B2 | 8/2011 | Mathe et al. | |
| 8,094,873 B2 | 1/2012 | Kelusky et al. | |
| 8,184,092 B2 | 5/2012 | Cox et al. | |
| 8,199,009 B2 | 6/2012 | Brunetti | |
| 8,203,454 B2 | 6/2012 | Knight et al. | |
| 8,213,680 B2 | 7/2012 | Fitzgibbon et al. | |
| 8,284,157 B2 | 10/2012 | Markovic et al. | |
| 8,290,249 B2 | 10/2012 | Mathe et al. | |
| 8,295,542 B2 | 10/2012 | Albertson et al. | |
| 8,334,842 B2 | 12/2012 | Markovic et al. | |
| 8,340,432 B2 | 12/2012 | Mathe et al. | |
| 8,351,652 B2 | 1/2013 | Mathe | |
| 8,374,423 B2 | 2/2013 | Lee et al. | |
| 8,379,101 B2 | 2/2013 | Mathe et al. | |
| 8,385,596 B2 | 2/2013 | Latta et al. | |
| 8,457,353 B2 | 6/2013 | Reville et al. | |
| 8,465,108 B2 | 6/2013 | Markovic et al. | |
| 8,565,479 B2 | 10/2013 | Gurman et al. | |
| 8,570,373 B2 | 10/2013 | Variyath et al. | |
| 8,652,038 B2 | 2/2014 | Tran et al. | |
| 8,930,040 B2 | 1/2015 | Gompert et al. | |
| 2003/0058111 A1 | 3/2003 | Lee et al. | |
| 2004/0193413 A1 | 9/2004 | Wilson et al. | |
| 2005/0203384 A1 | 9/2005 | Sati et al. | |
| 2005/0255434 A1 | 11/2005 | Lok et al. | |
| 2005/0267354 A1 | 12/2005 | Marquart et al. | |
| 2006/0052684 A1 | 3/2006 | Takahashi et al. | |
| 2006/0267781 A1 | 11/2006 | Coulter | |
| 2007/0016008 A1 | 1/2007 | Schoenefeld | |
| 2007/0046649 A1* | 3/2007 | Reiner | G06F 3/03545 345/173 |
| 2007/0118400 A1 | 5/2007 | Morita et al. | |
| 2008/0097176 A1* | 4/2008 | Music | A61B 5/7475 600/323 |
| 2008/0104547 A1 | 5/2008 | Morita et al. | |
| 2008/0114614 A1 | 5/2008 | Mahesh et al. | |
| 2008/0114615 A1 | 5/2008 | Mahesh et al. | |
| 2008/0170749 A1 | 7/2008 | Albertson et al. | |
| 2008/0170776 A1* | 7/2008 | Albertson | G06F 21/35 382/154 |
| 2009/0146848 A1 | 6/2009 | Ghassabian | |
| 2009/0189981 A1* | 7/2009 | Siann | H04N 7/183 348/143 |
| 2009/0195382 A1 | 8/2009 | Hall | |
| 2009/0198696 A1* | 8/2009 | Banks | G06F 19/322 |
| 2009/0237247 A1 | 9/2009 | Brunetti et al. | |
| 2009/0259113 A1 | 10/2009 | Liu et al. | |
| 2011/0007139 A1 | 1/2011 | Brunetti | |
| 2011/0037840 A1 | 2/2011 | Hiltl et al. | |
| 2011/0118752 A1 | 5/2011 | Itkowitz et al. | |
| 2011/0118753 A1 | 5/2011 | Itkowitz et al. | |
| 2011/0153361 A1 | 6/2011 | Hanina et al. | |
| 2011/0157480 A1 | 6/2011 | Curl | |
| 2011/0160578 A1 | 6/2011 | Tripathi et al. | |
| 2011/0173204 A1 | 7/2011 | Murillo et al. | |
| 2011/0213342 A1 | 9/2011 | Tripathi et al. | |
| 2011/0227741 A1 | 9/2011 | Jeon | |
| 2011/0251478 A1 | 10/2011 | Wieczorek | |
| 2011/0282141 A1 | 11/2011 | Itkowitz et al. | |
| 2011/0295078 A1 | 12/2011 | Reid et al. | |
| 2012/0059671 A1 | 3/2012 | Park et al. | |
| 2012/0071891 A1 | 3/2012 | Itkowitz et al. | |
| 2012/0071892 A1 | 3/2012 | Itkowitz et al. | |
| 2012/0086827 A1 | 4/2012 | Hanina et al. | |
| 2012/0116986 A1 | 5/2012 | Ault | |
| 2012/0154582 A1 | 6/2012 | Johnson et al. | |
| 2012/0172129 A1 | 7/2012 | Padovani et al. | |
| 2012/0185094 A1* | 7/2012 | Rosenstein | B25J 11/009 700/259 |
| 2012/0212582 A1 | 8/2012 | Deutsch | |
| 2012/0329420 A1* | 12/2012 | Zotti | H04M 1/72541 455/404.2 |
| 2013/0024382 A1* | 1/2013 | Dala | G06F 19/322 705/51 |
| 2013/0173300 A1 | 7/2013 | Hyde et al. | |
| 2013/0214925 A1* | 8/2013 | Weiss | G08B 25/001 340/539.11 |
| 2014/0009378 A1* | 1/2014 | Chew | G06F 3/017 345/156 |
| 2014/0049465 A1* | 2/2014 | Tremaine | G06F 3/017 345/156 |
| 2014/0096091 A1* | 4/2014 | Reid | G06F 19/3462 715/863 |
| 2014/0132728 A1 | 5/2014 | Verano et al. | |
| 2015/0081135 A1 | 3/2015 | Gompert et al. | |
| 2015/0302539 A1 | 10/2015 | Mazar et al. | |

FOREIGN PATENT DOCUMENTS

| | | |
|---|---|---|
| JP | 2007-58625 A | 3/2007 |
| WO | WO-2011/011454 A1 | 1/2011 |
| WO | WO-2013/184832 A2 | 12/2013 |

OTHER PUBLICATIONS

European Supplementary Search Report issued in EP 13842428.8, dated Apr. 26, 2016 (8 pages).

Notification of Reasons for Refusal issued in related Japanese Patent Application No. 2015-534750 dated Oct. 5, 2017 (6 pages).

* cited by examiner

EXAMPLE HAND / FINGER GESTURES
- WAVING
- MAKING A FIST
- SHAKING A FIST
- THUMBS UP
- SPREAD FINGERS
- DISPLAYING A COUNT
- POINTING
- MOVING HANDS TOGETHER
- PULLING HANDS APART
- WRIST TAP

FIG. 5

EXAMPLE HEAD / FACIAL GESTURES
- NODDING
- BOBBING
- SHAKING SIDE-TO-SIDE (E.G. "NO")
- SHAKING UP AND DOWN (E.G. "YES")
- BLINKING
- MOUTH OPENING / CLOSING
- TONGUE OUT
- EYEBROWS UP / DOWN
- EYES OPEN / CLOSED

FIG. 6

SYSTEMS AND METHODS FOR THREE-DIMENSIONAL INTERACTION MONITORING IN AN EMS ENVIRONMENT

CROSS-REFERENCE TO RELATED APPLICATIONS

This application claims the benefit of U.S. Provisional Patent Application Ser. No. 61/707,671, filed on Sep. 28, 2012, and of U.S. Provisional Patent Application Ser. No. 61/707,665, filed on Sep. 28, 2012, both of which are incorporated herein by reference in their entireties for all purposes.

TECHNICAL FIELD

Embodiments of the present invention relate generally to gesture recognition and three-dimensional interaction tracking in an emergency medical services environment.

BACKGROUND

In an emergency medical services ("EMS") or first responder environment, caregivers must often focus more acutely on patient care in a shorter amount of time and with a greater number of uncertainties and variables than their counterparts in a hospital setting. Creating a record of the EMS caregiver's encounter with a patient, however, remains important. Manual input of information into patient charting systems (e.g. by typing or by writing) can sometimes take valuable time and attention away from patient care, can be distracting, and can often be inaccurately recreated from memory after an EMS encounter.

SUMMARY

Example 1 includes a method for gesture recognition in an emergency response environment according to embodiments of the present invention includes receiving visual information about at least a portion of a human body from at least one sensor; maintaining an emergency encounter record; monitoring the visual information to determine movements of the at least the portion of the human body; recognizing an occurrence of a gesture based on the movements of the at least the portion of the human body; and recording an entry in the emergency encounter record based on the occurrence of the gesture.

Example 2 includes the method of Example 1, wherein the gesture is an artificial gesture.

Example 3 includes the method of any of Examples 1-2, wherein the gesture is a natural gesture.

Example 4 includes the method of any of Examples 1-3, wherein the at least the portion of the human body is a hand of the human body.

Example 5 includes the method of any of Examples 1-4, wherein the at least the portion of the human body comprises one or more digits of the hand of the human body.

Example 6 includes the method of any of Examples 1-5, wherein the at least the portion of the human body is a head of the human body.

Example 7 includes the method of any of Examples 1-6, wherein the entry comprises a time of the occurrence of the gesture.

Example 8 includes the method of any of Examples 1-7, wherein the entry further comprises an identification of the gesture.

Example 9 includes the method of any of Examples 1-8, wherein the entry comprises the visual information received corresponding to a time of the occurrence of the gesture.

Example 10 includes the method of any of Examples 1-9, the method further comprising receiving audio information, wherein the entry comprises the audio information received corresponding to the time of the occurrence of the gesture.

Example 11 includes the method of any of Examples 1-10, further comprising: determining an occurrence of a condition other than the gesture; and recording the entry in the emergency encounter record only when the occurrence of the condition coincides with the occurrence of the gesture.

Example 12 includes the method of any of Examples 1-11, wherein the gesture is a first gesture, and wherein the condition is a second gesture.

Example 13 includes the method of any of Examples 1-12, wherein the condition is a position or location of the human body with respect to the emergency response environment.

Example 14 includes the method of any of Examples 1-13, wherein the at least the portion of the human body is a first portion of the human body, wherein the gesture is a first gesture, the method further comprising: receiving visual information about a second portion of the human body from the at least one sensor; monitoring the visual information to determine movements of the second portion of the human body; recognizing an occurrence of a second gesture based on the movements of the second portion of the human body; and recording the entry in the emergency encounter record based on the occurrence of the first gesture and the occurrence of the second gesture.

Example 15 includes the method of any of Examples 1-14, wherein recording the entry comprises recording the entry in the emergency encounter record only when the first and second gestures coincide.

Example 16 includes the method of any of Examples 1-15, wherein the first portion of the human body is a hand, and wherein the second portion of the human body is a head.

Example 17 includes the method of any of Examples 1-16, wherein the first portion of the human body is a first hand, and wherein the second portion of the human body is a second hand.

Example 18 includes the method of any of Examples 1-17, wherein the human body is a patient being treated in the emergency response environment.

Example 19 includes the method of any of Examples 1-18, wherein the human body is a caregiver who is treating a patient in the emergency response environment.

Example 20 includes a system for gesture recognition in an emergency response environment according to embodiments of the present invention includes: at least one sensor configured to receive visual information about at least a portion of a human body; and a control system communicably coupled to the at least one sensor, the control system configured to: maintain an emergency encounter record; monitor the visual information to determine movements of the at least the portion of the human body; recognize an occurrence of a gesture based on the movements of the at least the portion of the human body; and record an entry in the emergency encounter record based on the occurrence of the gesture.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 illustrates a table listing various hand and finger gestures that may be recognized by the system of FIG. 4, according to embodiments of the present invention.

FIG. 6 illustrates a table listing various head and facial gestures that may be recognized by the system of FIG. 4, according to embodiments of the present invention.

Figure 1:
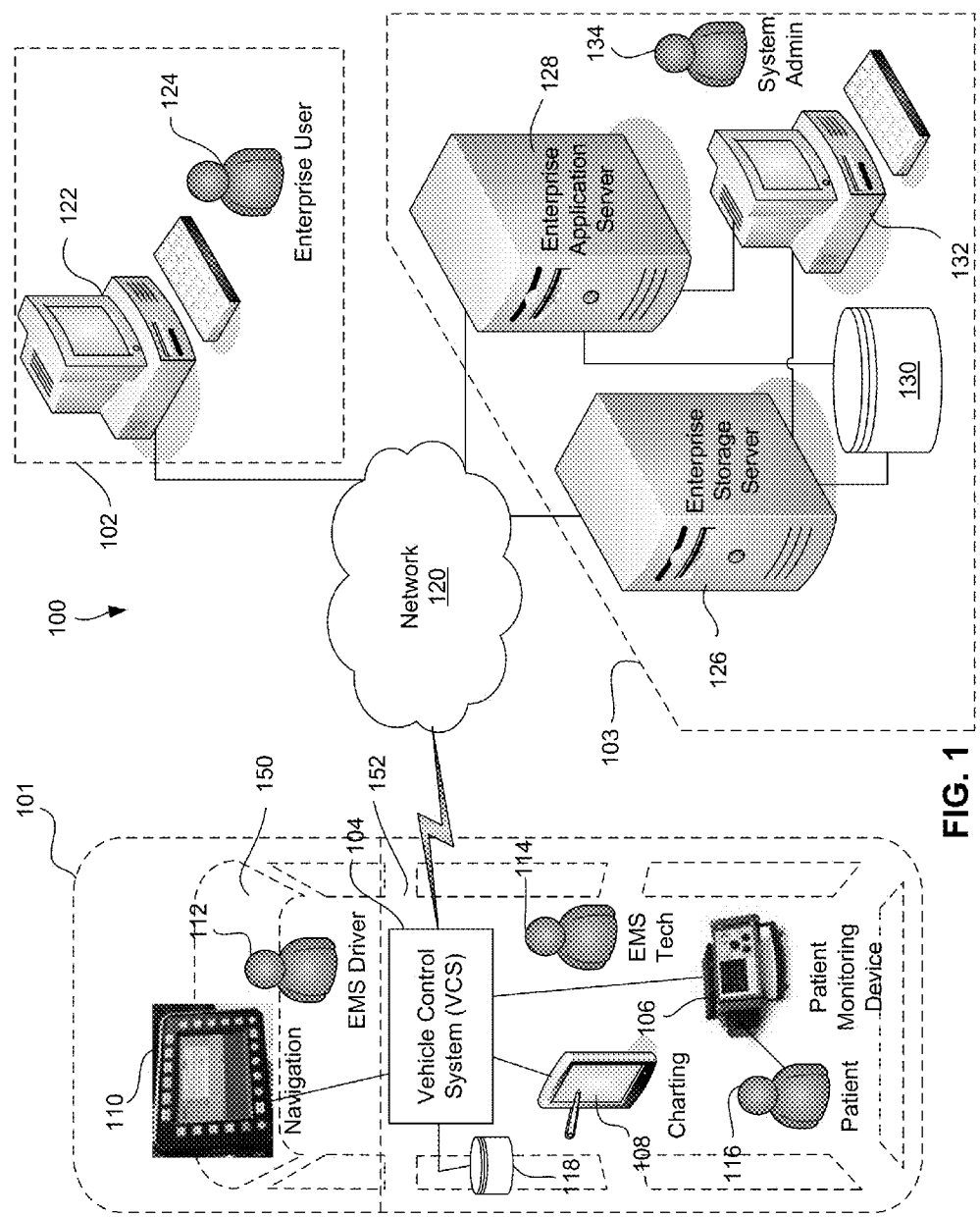
FIG. 1 illustrates an emergency response environment with a vehicle control system communicably coupled to other devices, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As illustrated in FIG. 1, a system 100 according to embodiments of the present invention performs advanced data management, integration and presentation of EMS data from multiple different devices. System 100 includes a mobile environment 101, an enterprise environment 102, and an administration environment 103. Devices within the various environments 101, 102, 103 may be communicably coupled via a network 120, such as, for example, the Internet. System 100 is further described in Patent Cooperation Treaty Application Publication No. WO 2011/011454, published on Jan. 27, 2011, which is incorporated herein by reference in its entirety for all purposes.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network, or direct coupling.

According to embodiments of the present invention, the mobile environment 101 is an ambulance or other EMS vehicle—for example a vehicular mobile environment (VME). The mobile environment may also be the local network of data entry devices as well as diagnostic and therapeutic devices established at time of treatment of a patient or patients in the field environment—the "At Scene Patient Mobile Environment" (ASPME). The mobile environment may also be a combination of one or more of VMEs and/or ASPMEs. The mobile environment may include a navigation device 110 used by the driver 112 to track the mobile environment's position 101, locate the mobile environment 101 and/or the emergency location, and locate the transport destination, according to embodiments of the present invention. The navigation device 110 may include a Global Positioning System ("GPS"), for example. The navigation device 110 may also be configured to perform calculations about vehicle speed, the travel time between locations, and estimated times of arrival. According to embodiments of the present invention, the navigation device 110 is located at the front of the ambulance to assist the driver 112 in navigating the vehicle. The navigation device 110 may be, for example, a RescueNet® Navigator onboard electronic data communication system available from ZOLL Data Systems of Broomfield, Colo.

As illustrated in FIG. 1, a patient monitoring device 106 and a patient charting device 108 are also often used for patient care in the mobile environment 101, according to embodiments of the present invention. The EMS technician 114 attaches the patient monitoring device 106 to the patient 116 to monitor the patient 116. The patient monitoring device 106 may be, for example, a defibrillator device with electrodes and/or sensors configured for attachment to the patient 116 to monitor heart rate and/or to generate electrocardiographs ("ECG's"), according to embodiments of the present invention. The patient monitoring device 106 may also include sensors to detect or a processor to derive or calculate other patient conditions. For example, the patient monitoring device 106 may monitor, detect, treat and/or derive or calculate blood pressure, temperature, respiration rate, blood oxygen level, end-tidal carbon dioxide level, pulmonary function, blood glucose level, and/or weight, according to embodiments of the present invention. The patient monitoring device 106 may be a Zoll E-Series® or X-Series defibrillator available from Zoll Medical Corporation of Chelmsford, Mass., according to embodiments of the present invention. A patient monitoring device may also be a patient treatment device, or another kind of device that includes patient monitoring and/or patient treatment capabilities, according to embodiments of the present invention.

The patient charting device 108 is a device used by the EMS technician 114 to generate records and/or notes about the patient's 116 condition and/or treatments applied to the patient, according to embodiments of the present invention. For example, the patient charting device 108 may be used to note a dosage of medicine given to the patient 116 at a particular time. The patient charting device 108 and/or patient monitoring device 106 may have a clock, which may be synchronized with an external time source such as a network or a satellite to prevent the EMS technician from having to manually enter a time of treatment or observation (or having to attempt to estimate the time of treatment for charting purposes long after the treatment was administered), according to embodiments of the present invention. The patient charting device 108 may also be used to record biographic and/or demographic and/or historical information about a patient, for example the patient's name, identification number, height, weight, and/or medical history, according to embodiments of the present invention. According to embodiments of the present invention, the patient charting device 108 is a tablet PC, such as for example the TabletPCR component of the RescueNet® ePCR Suite available from Zoll Data Systems of Broomfield, Colo. According to some embodiments of the present invention, the patient charting device 108 is a wristband or smartphone such as an Apple iPhone or iPad with interactive data entry interface such as a touch screen or voice recognition data entry that may be communicably connected to the VCS 104 and tapped to indicate what was done with the patient 116 and when it was done.

The navigation device 110, the charting device 108, and the monitoring device 106 are each separately very useful to the EMS drivers 112 and technicians 114 before, during, and after the patient transport. A vehicle control system ("VCS") 104 receives, organizes, stores, and displays data from each device 108, 110, 112 to further enhance the usefulness of each device 108, 110, 112 and to make it much easier for the EMS technician 114 to perform certain tasks that would normally require the EMS technician 114 to divert visual and manual attention to each device 108, 110, 112 separately, according to embodiments of the present invention. In other words, the VCS centralizes and organizes information that would normally be de-centralized and disorganized, according to embodiments of the present invention.

The VCS 104 is communicably coupled to the patient monitoring device 106, the patient charting device 108, and the navigation device 110, according to embodiments of the present invention. The VCS 104 is also communicably coupled to a storage medium 118. The VCS 104 may be a touch-screen, flat panel PC, and the storage medium 118 may be located within or external to the VCS 104, according to embodiments of the present invention. The VCS 104 may include a display template serving as a graphical user interface, which permits the user (e.g. EMS tech 114) to select different subsets and/or display modes of the information gathered from and/or sent to devices 106, 108, 110, according to embodiments of the present invention.

Some embodiments of the present invention include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware. In addition, some embodiments of the present invention may be performed or implemented, at least in part (e.g., one or more modules), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present invention may incorporate one or more of these systems, or portions thereof.

Figure 2:
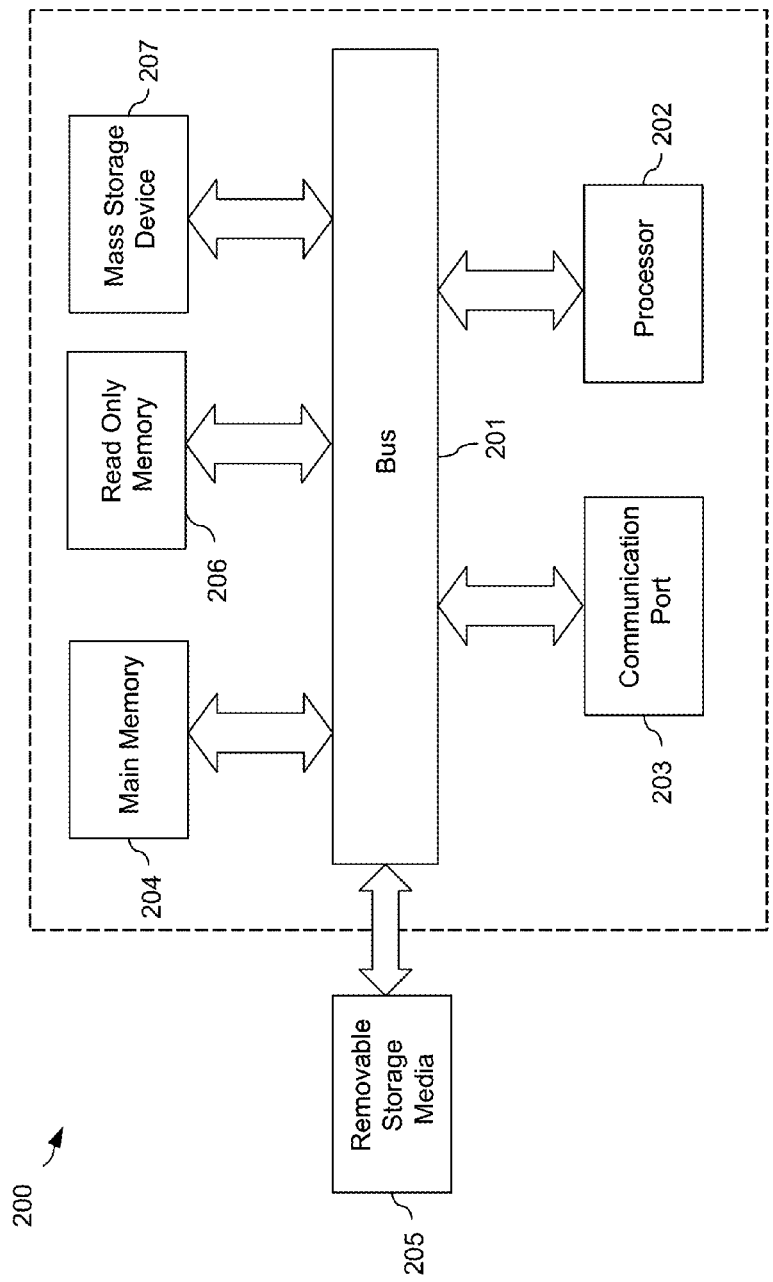
FIG. 2 illustrates a computer system, according to embodiments of the present invention.

As such, FIG. 2 is an example of a computer system 200 with which embodiments of the present invention may be utilized. According to the present example, the computer system includes a bus 201, at least one processor 202, at least one communication port 203, a main memory 24, a removable storage media 205, a read only memory 206, and a mass storage 207.

Processor(s) 202 can be any known processor, such as, but not limited to, an Intel® Itanium® or Itanium 2® processor(s), or AMD® Opteron® or Athlon MP® processor(s), or Motorola® lines of processors. Communication port(s) 203 can be any of an RS-232 port for use with a modem based dialup connection, a 10/100 Ethernet port, or a Gigabit port using copper or fiber, for example. Communication port(s) 203 may be chosen depending on a network such a Local Area Network (LAN), Wide Area Network (WAN), or any network to which the computer system 200 connects. Main memory 204 can be Random Access Memory (RAM), or any other dynamic storage device(s) commonly known to one of ordinary skill in the art. Read only memory 206 can be any static storage device(s) such as Programmable Read Only Memory (PROM) chips for storing static information such as instructions for processor 202, for example.

Mass storage 207 can be used to store information and instructions. For example, hard disks such as the Adaptec® family of SCSI drives, an optical disc, an array of disks such as RAID (e.g. the Adaptec family of RAID drives), or any other mass storage devices may be used, for example. Bus 201 communicably couples processor(s) 202 with the other memory, storage and communication blocks. Bus 201 can be a PCI/PCI-X or SCSI based system bus depending on the storage devices used, for example. Removable storage media 205 can be any kind of external hard-drives, floppy drives, flash drives, IOMEGA® Zip Drives, Compact Disc—Read Only Memory (CD-ROM), Compact Disc—Re-Writable (CD-RW), or Digital Video Disk—Read Only Memory (DVD-ROM), for example. The components described above are meant to exemplify some types of possibilities. In no way should the aforementioned examples limit the scope of the invention, as they are only exemplary embodiments.

Figure 3:
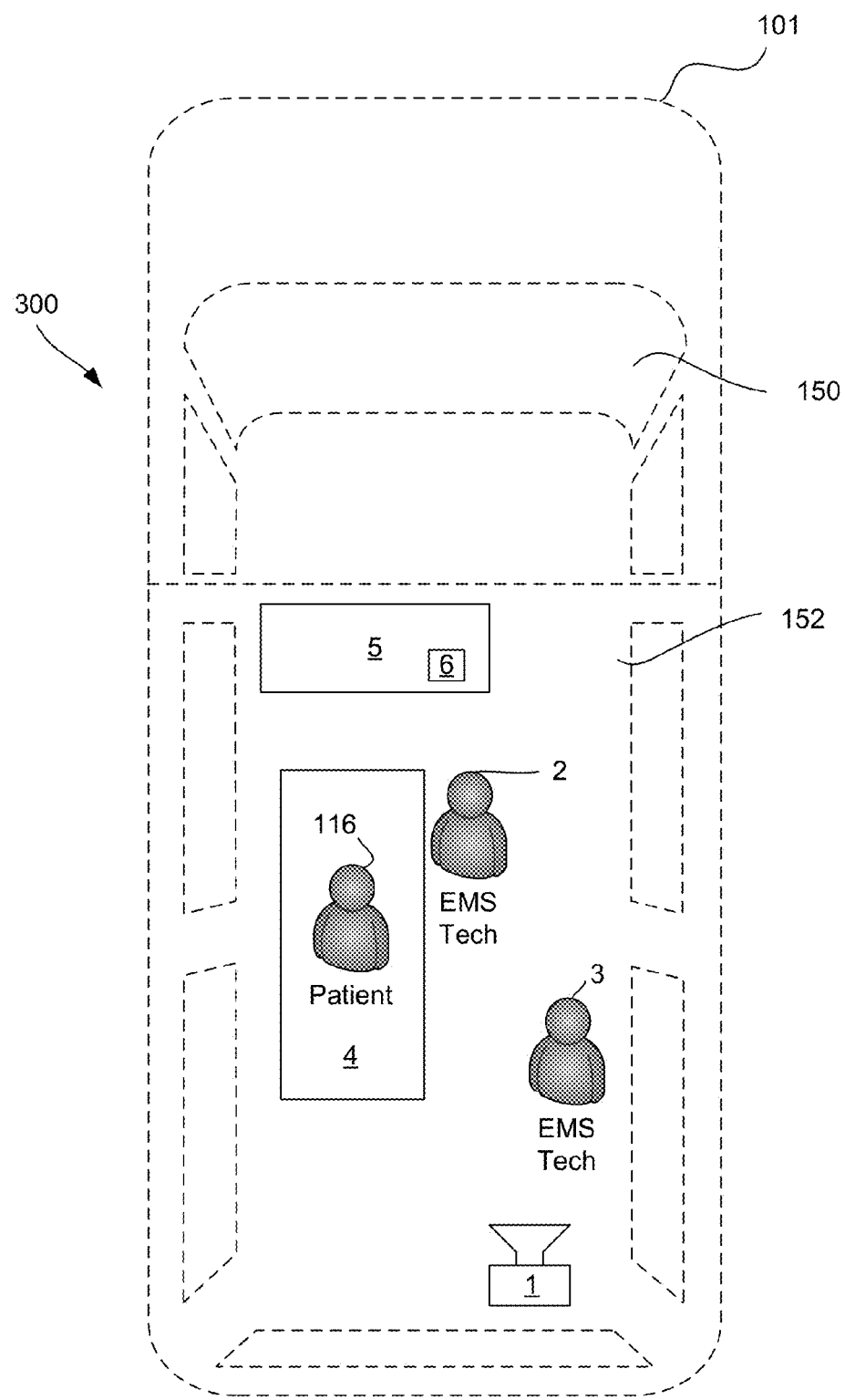
FIG. 3 illustrates an emergency response environment with a system that monitors three-dimensional interaction, according to embodiments of the present invention.

FIG. 3 illustrates an emergency response environment with a system 300 that monitors three-dimensional interaction, according to embodiments of the present invention. System 300 includes a sensor or sensor array 1. Sensor 1 may be a camera, video camera, or other imaging device capable of collecting visual information. According to some embodiments of the present invention, sensor 1 is a sensor array that includes an image capture device, for example a color image capture device, as well as a depth determining device, for example an infrared emitter and infrared depth sensor. Sensor 1 may also include an audio capture device. For example, sensor 1 may be a sensor array such as a Kinect® sensor array available from Microsoft Corporation. Sensor 1 may also or alternatively be a LEAP™ device available from Leap Motion, Inc. Sensor 1 may be, or include, a wide variety of hardware that permits collection of visual, depth, audio, and color information and the like, according to embodiments of the present invention.

Sensor 1 may be placed within an emergency response environment, for example in the back 152 of an ambulance 101, such that activities of the patient 116 and/or crew members 2, 3 are at least partially within its field of view. For example, sensor 1 may be mounted on a wall or ceiling of the back compartment 152 of the ambulance 101. The sensor 1 may also include, within its field of view, a patient support 4, such as a bed, cot, or stretcher, upon which a patient 116 is laying and/or being treated. The back 152 of the ambulance 101 may further include a supply cabinet 5, for example a medicine cabinet or narcotics cabinet, which may be stocked with medicines, for example narcotic 6.

Figure 4:
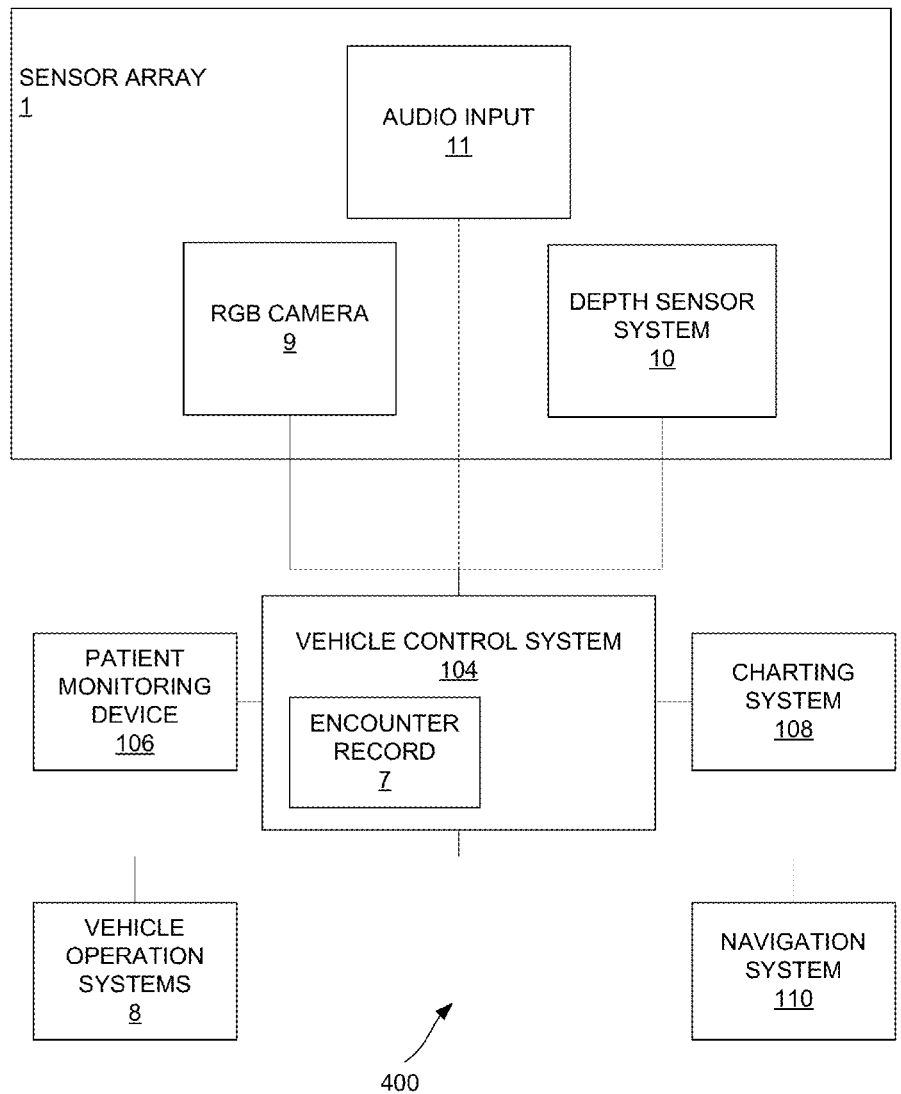
FIG. 4 illustrates a system including a vehicle control system and a sensor array, according to embodiments of the present invention.

FIG. 4 illustrates a system including a vehicle control system 104 communicably coupled with a sensor array 1, according to embodiments of the present invention. Sensor array 1 may include an imaging device 9, a depth sensor system 10, and/or an audio input 11, according to embodiments of the present invention. VCS 104 may also be communicably coupled with a patient monitoring device 106, a charting system 108, a navigation system 110, and vehicle operations systems 8. The vehicle operation systems 8 may include sensors and controllers installed in the vehicle relating to vehicle safety and/or operation, including both manufacturer-installed and aftermarket devices, for example vehicle speed sensors, seatbelt detectors, accelerometers, and other vehicle- and safety-related devices, including without limitation those described in U.S. Provisional Patent Application Ser. No. 61/656,527, filed on Jun. 7, 2012, which is incorporated by reference herein in its entirety for all purposes.

Vehicle control system 104 may be configured to create, maintain, and/or update an encounter record 7, which may be stored locally in an emergency response environment (for example in database 118) and/or remotely on an enterprise database 130. The encounter record 7 may include information obtained by the vehicle control system 104 and each of the devices to which VCS 104 is communicably coupled. Records in the encounter record 7 may be specific to an encounter with a particular patient 116, and/or a particular dispatch of the vehicle 101, for example.

The VCS 104 may be configured to track interactions in the emergency response environment, for example interactions by and among caregivers 2, 3, and patient 4 and/or objects in the emergency response environment. The VCS 104 may be configured to receive color images and depth information from within a field of view of the sensor array 1. The VCS 104 may also be configured to maintain an emergency encounter record 7, either locally and/or remotely. The VCS 104 monitors a position of an object and/or movement of the object in the emergency response environment based on the color images and depth information received by the sensor array 1. For example, the sensor array 1 may be a Kinect® sensor array, and the VCS 104 may include software that receives data from the sensor array 1 to detect or approximate movements and locations of human bodies and their respective linkages (skeletal joints and bones) in three-dimensional space.

As such, the VCS 104 can distinguish between different humans in the field of view of the sensor 1, and can monitor or observe the movements of two or more of such humans in the field of view. According to some embodiments of the present invention, the VCS 104 is configured to recognize which of the humans is a patient and which is a caregiver. For example, VCS 104 may recognize a human as a patient by observing that the particular human is laying relatively still on the patient support 4, while another human is an EMS technician 2 because the other human is standing up or moving around the back of the ambulance 101. The VCS 104 may be configured to track or monitor three-dimensional movements of one or more humans in the emergency response environment by approximating elements of their basic skeletal structure and, as such, can determine when two humans are in contact or close proximity. For example, the VCS 104 can determine when a hand or arm of the EMS technician 2 reaches over and touches an area of the patient's 116 body, according to embodiments of the present invention.

Any or all of the information received by the VCS 104 from the sensor array 1, as well as any additional data or information derived from such sensor information, may be stored to the encounter record 7. Such information may also be stored to the encounter record 7 in a manner that correlates it with other data in the encounter record 7 from other devices, for example records in the encounter record 7 may include a time index and/or a patient identification.

According to embodiments of the present invention, the VCS 104 is configured to record into the emergency encounter record 7 an occurrence of a condition. Such condition may be based on the position of the object and/or the movement of the object. For example, the object may be a human, and the VCS 104 may monitor the human's movement (or a skeletal approximation thereof) in three-dimensional space, and make an entry in the encounter record 7 when the human or part of the human intersects a certain location (e.g. within the ambulance 101), or remains in a particular location for a certain amount of time, or intersects or nears another object. The VCS 104 may be configured to make an entry to the encounter record 7 when one object (e.g. a human) comes within a certain distance of another object (e.g. another human), for example a zero or minimal distance at which the first object is touching the second object. As such, the VCS 104 may be configured to mark the encounter record 7 when a caregiver 2 or 3 approached the patient 116 and/or touched the patient 116, or when an object approached or touched the patient 116.

The VCS 104 may be configured to update the encounter record 7 in various ways based on the observance of a condition based on three-dimensional visual and position data. For example, the VCS 104 may be configured to enter into the encounter record 7 a time at which the condition occurred, and/or an identification of the condition or type of condition that occurred, and/or other data coinciding with the occurrence of the condition, for example video data or color images covering the time or time range when the condition occurred. In some cases, the VCS 104 receives streaming clinical data about a patient 116, for example from a defibrillator or other patient monitoring device 106 communicably coupled to the patient, and correlates at least a portion of the streaming clinical data in the emergency encounter record 7 with the occurrence of the condition based on the sensor's 1 visual data. According to embodiments of the present invention, correlating some or all of the streaming clinical data includes flagging some or all of the streaming clinical data that corresponds to a time of the occurrence of the condition.

Figure 7:
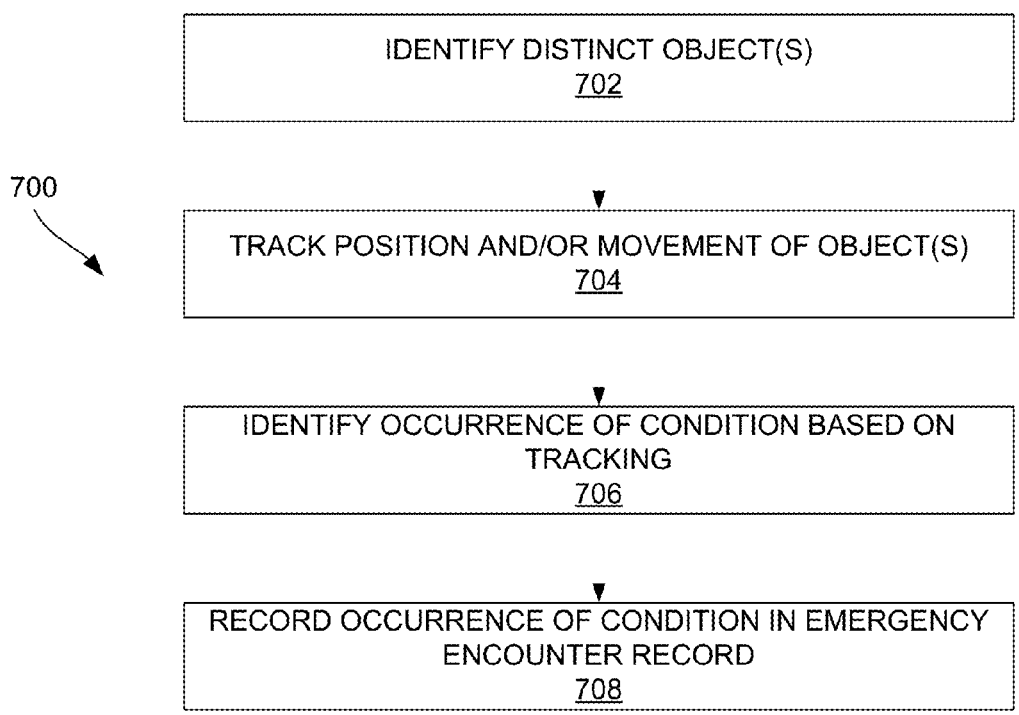
FIG. 7 depicts a flow chart illustrating a method for monitoring three-dimensional interaction in an emergency response environment, according to embodiments of the present invention.

FIG. 7 illustrates a flow chart 700 showing the recording of an occurrence of a condition based on three-dimensional position and shape visual data, according to embodiments of the present invention. One or more distinct objects are identified (block 702), for example by VCS 104 and sensor 1. The position and/or movement of the one or more objects are tracked or otherwise monitored or modeled (block 704), and based on such tracking the VCS 104 identifies the occurrence of a condition (block 706). The occurrence of the condition, or information about the condition, is recorded in the patient encounter record 7 (block 708).

Figure 8:
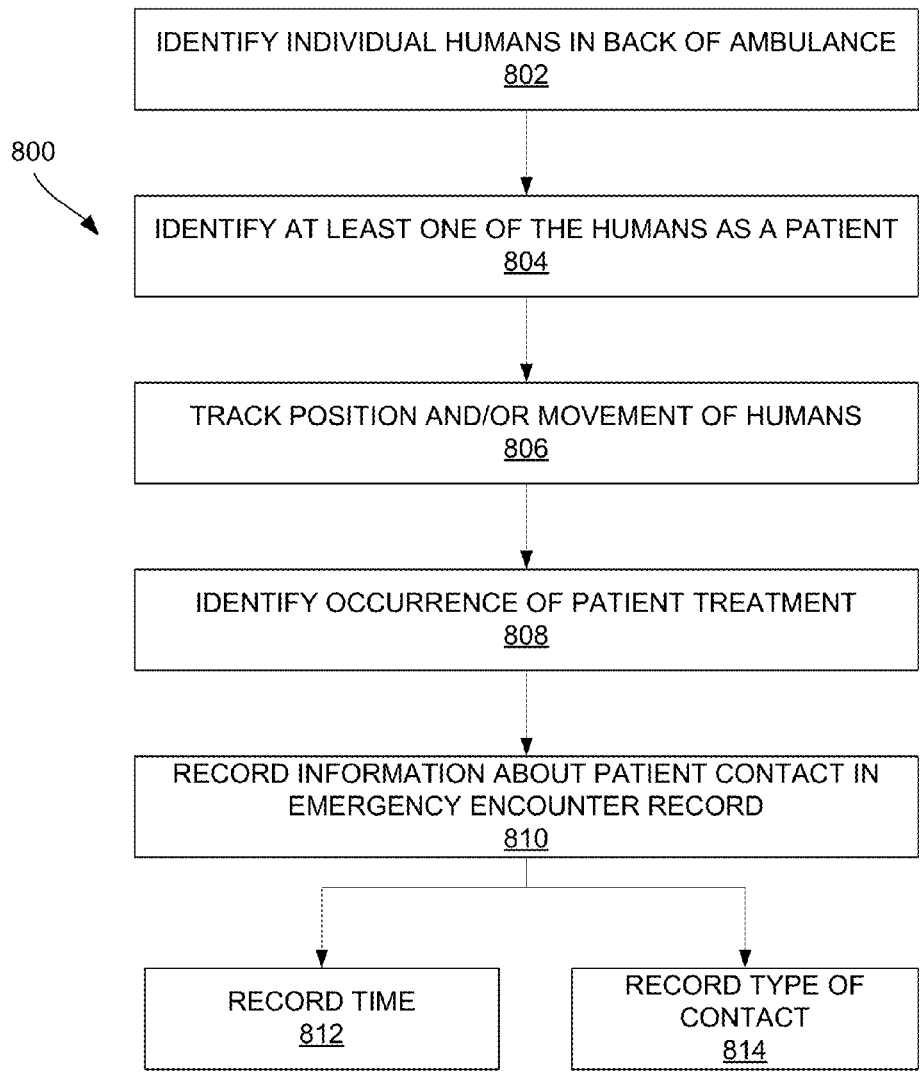
FIG. 8 depicts a flow chart illustrating a method for monitoring three-dimensional interaction of a caregiver with a patient in an emergency response environment, according to embodiments of the present invention.

FIG. 8 illustrates a flow chart 800 describing a similar method in greater detail, according to embodiments of the present invention. An individual human or distinct humans are identified in an emergency response environment, for example the back of an ambulance (block 802). At least one of the humans is identified as a patient (block 804). The position and/or movement of the one or more humans is observed or tracked or otherwise modeled (block 806), and based thereon the VCS 104 identifies the occurrence of a condition, for example the occurrence of patient treatment (block 808). Information about the patient contact may be recorded in the encounter record 7 (block 810), for example by recording a time or time range at which the condition (e.g. treatment) occurred (block 812), and/or by recording a type of contact (e.g. treatment) which occurred (block 814).

For example, if the sensor 1 data supplied to the VCS 104 was interpreted by the VCS 104 as a caregiver's 2 hand going to the head or mouth area of the patient 116, the VCS 104 may update the encounter record 7 to reflect that an oral medication was or may have been administered to the patient 116, and the particular time which this occurred. Alternatively, or in addition, the VCS 104 may be configured to prompt the EMS technician 2 or other caregiver at a later time, for example after the emergency encounter or at the end of a standard shift, to confirm or validate the perceived interactions or conditions that were entered into the patient encounter record 7. For example, the VCS 104 might observe the occurrence of the EMS technician's 2 hand going to the face of the patient 116 and flag such occurrence as the possible administration of an oral medication, but when prompting the EMS technician 2 for later confirmation, may give the EMS technician 2 the ability to edit the observation to reflect that the interaction was instead a turning of the head of the patient, or some other reason for why the caregiver 2 contacted the patient 116.

Figure 9:
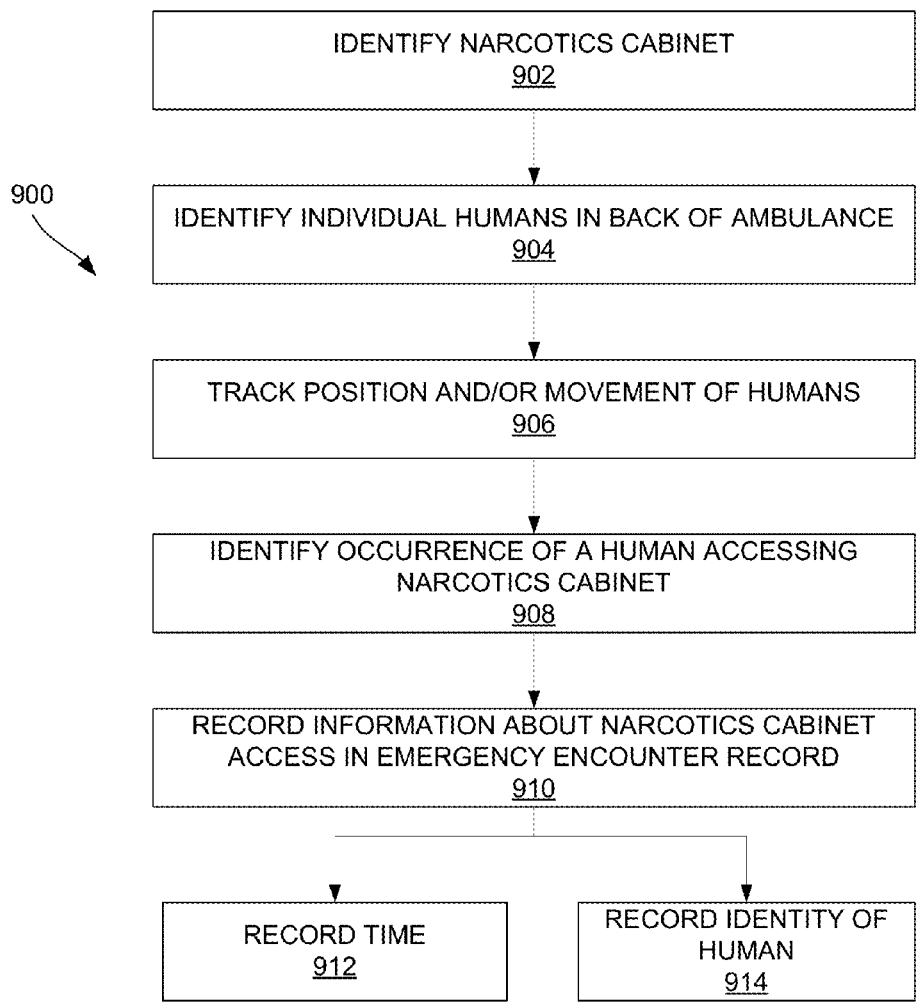
FIG. 9 depicts a flow chart illustrating a method for monitoring three-dimensional interaction in an emergency response environment for inventory control, according to embodiments of the present invention.

FIG. 9 depicts a flow chart 900 illustrating a method for monitoring three-dimensional interaction in an emergency response environment for inventory control, according to embodiments of the present invention. The VCS 104 may identify a particular location within the emergency response environment, for example a supply cabinet 5, using sensor 1 and known information about the environment (block 902). The VCS 104 may also be configured for customization regarding the locations of certain items in the emergency response environment. For example, during an initialization and/or configuration protocol, the VCS 104 may prompt the user to run the user's finger or hand around an outer perimeter of a supply cabinet 5 and/or a door thereto, so that the VCS 104 can log the three-dimensional position of the supply cabinet 5. Such cabinet 5 may be, for example, a narcotics cabinet 5 to which access is often controlled for safety and security reasons.

The VCS 104 may identify individual humans in the emergency response environment, for example the back of an ambulance (block 904), and track the position and/or movement of such humans (block 906). This may be done with visual and depth information received from the sensor array 1, according to embodiments of the present invention. Based on such visual and depth information received from the sensor array 1, the VCS 104 may also detect or track three-dimensional movement of an object in the emergency response environment, for example a non-human object. The VCS 104 may determine an occurrence of contact between the human body and the object (block 908), for example an occurrence of the human body or a portion thereof approaching and/or intersecting the narcotics cabinet 5. The VCS 104 may also record an entry in an emergency encounter record 7 based on the occurrence of the contact, for example a note that the cabinet 5 was accessed (block 910) along with a time (block 912) and/or an identity of the person who accessed the cabinet 5 (block 914). The VCS 104 may be configured to observe the occurrence of various different types of conditions of note. For example, the VCS 104 may be configured to detect an intersection of a human form with the area of the door or opening to the cabinet 5. The VCS 104 may be configured to detect that a shape that correlates to the shape of the narcotic medication 6 has gone from inside such area of the door or cabinet opening to outside such area.

VCS 104 may also be configured to note whether a human has an object in the human's hand as well as the shape and/or size of the object. The VCS 104 may further be configured to update an inventory database, based on the occurrence of the removal, to reflect that the narcotic medication has been used and needs restocking. Similar processes may be used to track the use of other objects and the inventory associated therewith, as well as to track in general the intersection of objects with humans and use thereby, according to embodiments of the present invention. According to some embodiments of the present invention, the occurrence of an access event to the particular cabinet 5 may further trigger other information gathering, for example it may trigger a camera on the inside of the cabinet 5 and/or another video camera elsewhere in the vehicle 101. The identity of each crew member accessing the cabinet 5 may be recorded in the encounter record 7, according to embodiments of the present invention.

Figure 10:
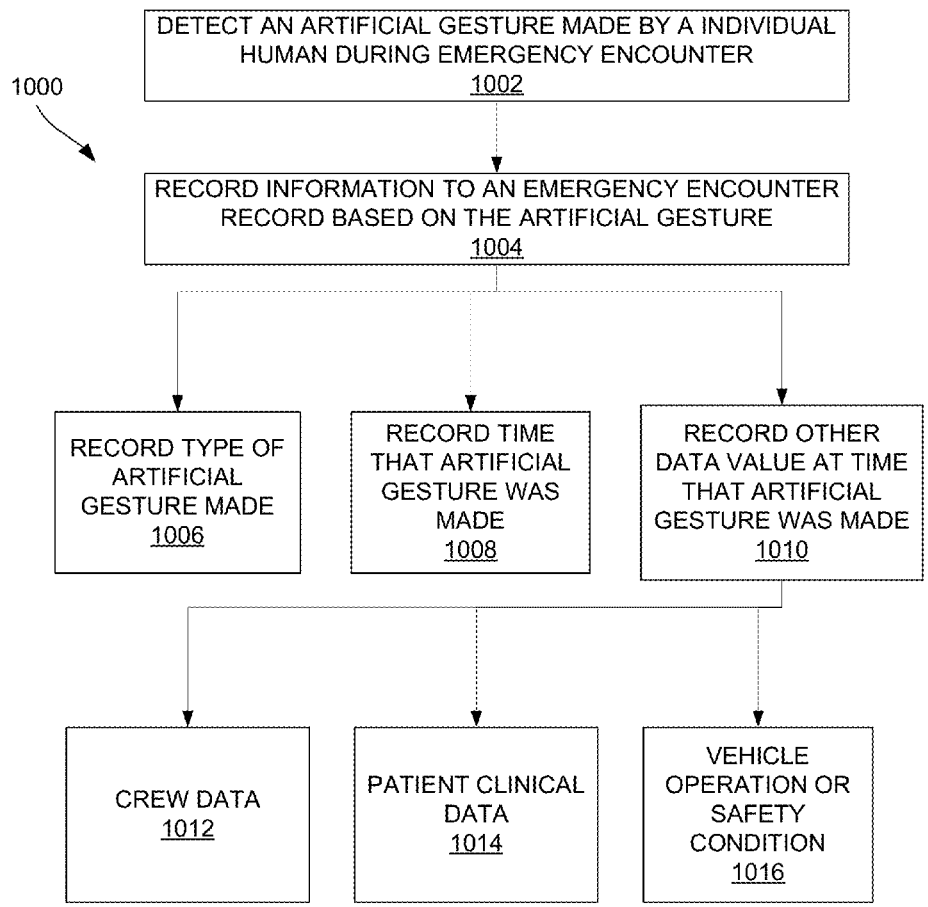
FIG. 10 depicts a flow chart illustrating a method for gesture recognition in an emergency response environment, according to embodiments of the present invention.

FIG. 10 depicts a flow chart 1000 illustrating a method for gesture recognition in an emergency response environment, according to embodiments of the present invention. While system 400, including VCS 104 and sensors 1, may be configured to track motions, positions, and interactions of humans and objects as described above, system 400 as well as VCS 104 and sensors 1 may also or alternatively be configured to monitor such visual information for the occurrence of gestures. In some cases, three-dimensional position and visual information may be used to monitor for gestures; in other cases, mere visual information may be used to detect gestures (e.g. based on pattern recognition or other visual cues or patterns). As such, sensor 1 may be one of a number of various types of sensors or sensor arrays.

VCS 104 may be configured to track an entire human body and/or one or more portions thereof to identify gestures being made, for example gestures being made by one or more hands and/or fingers or by the head and/or neck (block 1002). VCS 104 receives visual information about at least a portion of a human body from at least one sensor 1, and maintains the encounter record 7. The VCS 104 is configured to monitor the visual information to determine movements of the at least the portion of the human body (for example the hand or the head), and to recognize an occurrence of a gesture based on the movements of the at least the portion of the human body. For example, the VCS 104 recognizes one or more hand or finger gestures based on visual and/or depth information received by sensor 1, for example one or more hand or finger gestures listed in FIG. 5. The VCS 104 may also recognize one or more head or facial gestures based on visual and/or depth information received by sensor 1, for example one or more head or facial gestures listed in FIG. 6.

Examples of hand or finger gestures may include waving a hand or finger, making a fist, raising the fist, shaking the first, making the "thumbs up" signal, spreading fingers apart, displaying a count (e.g. zero, one, two, three, four, five, six, seven, eight, nine, or ten digits extended), pointing, moving hands together, pulling hands apart, and/or tapping on the wrist. Examples of head or facial gestures may include nodding the head, bobbing the head, shaking the head side-to-side as in the "no" gesture, shaking the head up and down as in the "yes" gesture, blinking, opening or closing the mouth, sticking the tongue out, raising or lowering eyebrows, and/or opening or closing the eyes.

When the VCS 104 recognizes a gesture, the VCS 104 records an entry in the emergency encounter record 7 based on the occurrence of the gesture (block 1004). Such a gesture may be artificial, or alternatively such a gesture may be natural. An artificial gesture is a gesture made by a human for the primary purpose of triggering the condition with VCS 104. As such, an artificial gesture may be a gesture that would not normally be made in the normal course of treating a patient 116 in an emergency response environment. For example, making a "thumbs up" signal is one example of an artificial gesture. A patient whose head is involuntarily bobbing is an example of a natural gesture, or a gesture which is not performed only to trigger VCS 104.

The entry which the VCS 104 makes in the patient encounter record 7 based on the recognition of the gesture may include information about the type of gesture made (block 1006), information about the time at which the gesture was made (block 1008), and/or information about other data values at the time the gesture was made (block 1010), for example information about the crew (block 1012), patient clinical data (block 1014), and vehicle operation or safety conditions (block 1016). For example, VCS 104 may be configured to write the patient's 116 current blood pressure reading to the encounter record 7 whenever VCS 104 receives visual and/or depth information from the sensor 1 indicating that the caregiver 2 attending to the patient 116 taps his or her left wrist with the right hand or fingers (tapping the location where a watch would normally be worn). Successive gestures may be used to take the VCS 104 down various pathways and/or treatment protocols, or to confirm previous gestures or options that become available because of those gestures. For example, the VCS 104 may be configured to record a blood pressure reading to the encounter record 7 when it identifies the wrist tapping gesture followed by a chest tapping gesture, and may be configured to record an ECG waveform signal to the encounter record 7 when it identifies the same wrist tapping gesture followed by a back-of-the-neck tapping gesture. The VCS 104 may also be configured to record in the encounter record 7 the audiovisual (e.g. video and/or audio) information received during or within a certain time range of the gesture, according to embodiments of the present invention.

According to some embodiments of the present invention, the VCS is configured to identify simultaneous occurrence of gestures, for example two or more gestures selected from FIG. 5, FIG. 6, or any other natural or artificial gestures. According to some embodiments of the present invention, the VCS 104 is configured to identify simultaneous occurrence of gestures along with position and/or movement information for entire human bodies or portions thereof, or simultaneous occurrence of other factors such as vehicle position along the ambulance route, patient vital signs, and/or vehicle speed. VCS 104 may also be configured to identify simultaneous occurrence of gestures by the same person, for example a different or similar gesture with each hand, or a hand and a head. For example, the VCS 104 may be configured to recognize a hand waiving gesture and to make a record in the encounter record 7 and notify the ambulance driver to slow down if the hand waiving gesture is received at a time when the vehicle speed is exceeding 60 miles per hour. In this way, the visually recognized gestures may be paired or correlated or combined with other information received by VCS 104, either in the creation of the condition which triggers a further event (such as writing to the encounter record 7 or creating a notification or some other action), or in the creation of the entry to the encounter record 7 itself (for example the types of information that would be flagged or gathered or otherwise noted upon occurrence of the condition).

According to some embodiments, the VCS 104 identifies (either in the encounter record 7 or for other devices) whether a patient is being transported by the vehicle 101, for example by determining whether a human figure is sitting on or laying on the patient support 4. The VCS 104 may also identify the position of a patient or a crew member, for example whether the patient or crew member is sitting or standing. The VCS 104 may also receive from sensor 1 information about structures beyond a normal emergency response environment, for example larger-scale depth images of emergency incidents such as buildings on fire, to aid in the location of emergency workers and/or victims.

Although one sensor 1 is shown and described, multiple sensors 1, either of the same type of different types, may be communicably coupled with VCS 104. Multiple sensors 1 may be used to expand the field or depth of view, or to collect similar information from a different viewing angle, in order to observe more objects or humans, or gather more detailed information about shapes and/or movements. And although sensor 1 is described as being mounted within a vehicle, sensor 1 or multiples thereof may alternatively be mounted on a device (for example a defibrillator taken to an emergency response scene) and/or on a person (for example on a crew member's helmet).

Embodiments of the present invention may also be used for charting and/or counting functions. Often, medics must reconstruct past events that occurred during patient treatment. Embodiments of the present invention improve accuracy and help to accurately document times at which various events occurred. For example, the VCS 104 may recognize boundaries of multiple cabinets or storage areas within an ambulance 101, and may log the times at which each storage area was accessed by a medic, as well as the identity (e.g. obtained from voice or body or facial recognition) of the medic who accessed the area. Such a "bounding volume" may be preprogrammed into VCS 104 and/or customized or initialized upon installation of VCS 104, sensor 1, and/or a new storage area. The VCS 104 may count a number of boxes on the floor of the ambulance to determine a number of items used in the encounter, and reconcile that with the medications and other durable goods charted for the patient encounter. The VCS 104 may then prompt the medic for additional information to help reconcile the encounter record 7.

As described above, the system 400 may also determine when a patient is being touched, either by another human or by an implement held by another human. This information may be used either during the patient encounter, or afterward, to determine whether inappropriate patient contact has occurred. The system 400 may determine when an IV is being started. System 400 may also use gesture-based charting, for example quick-logging with artificial gestures, to save time over manual entry or typing of such information. Embodiments of the present invention may also include voice recognition, which may filter out siren sounds or road sounds, and which may also provide feedback to the crew. Embodiments of the present invention may also be configured to identify crew members, for example through facial recognition, pattern recognition, name badge reading, skeletal modeling, habits or movements, or via another mechanism such as crew logins or RFID badges which are also communicably coupled to VCS 104. According to some embodiments of the present invention, the system 400 may be used for security monitoring, to detect the presence of unidentified or unwanted intruders in the vehicle 101.

According to some embodiments of the present invention, the system 400 may be used to begin tracking a person when the person makes a gesture or performs a certain activity, and then continue to track the same person after the gesture or activity, for a certain period of time or until another event occurs, for example another visual event. In some embodiments, the system 400 identifies an operator of a medical device using visual information; for example, a patient monitoring device 106, such as a defibrillator, may include a camera or other type of sensor array 1, and upon use of the device 106 the device 106 may observe visual characteristics of the person directly in front of the device 106 in order to identify the person or monitor or interpret activities of that person. The system 400 may also be configured to recognize or identify in its field of view equipment used by medical personnel, either by visual cues or otherwise, and may perform similar medical personnel identification or visual monitoring even when the camera or sensor array 1 is not in or near the device being used. Such multiple devices used by medical personnel may be wirelessly or otherwise communicably coupled with each other and/or with system 400, so that activities performed on various devices and by the personnel are correlated for a more complete patient record without requiring manual annotation, according to embodiments of the present invention. The system 400 may be mounted not only in a vehicle, such as the back of an ambulance, but system 400 and/or parts thereof may also be integrated into or mounted on a medical device, including a portable medical device such as a defibrillator.

The system 400 may also be configured to "remember" a person based on that person's gestures; for example, the system 400 may observe certain gestures performed by a person one day after the person identifies himself or herself to the system 400, and may then visually identify the same person the next day based on observing similar gestures, even if the person has not specifically identified himself or herself to the system 400 on the following occasion. The system 400 may also be configured to count the number of distinct individual people in a given area, according to embodiments of the present invention.

The system 400 may also be configured to monitor certain activities and to interpret various aspects of those activities, and even to provide feedback to the performer of the activities either in real time or in a later review. For example, the system 400 may monitor an EMS technician's twelve-lead placement on a patient, and/or may provide adaptive feedback, for example adaptive feedback to a person who is administering cardiopulmonary resuscitation. The system 400 may also be configured to identify a certain portion of the body, or an object held by a person, and to track the movement of the body part or object and record the tracked motion as writing. For example, an EMS technician could write numbers, letters, or words in the air using a finger, and the system 400 may be configured to record such movement as writing. The EMS technician may initiate such "air writing" recording mode with a gesture or other activation; in other embodiments, the system 400 automatically recognizes such "air writing" based on the absence of other objects with which the user's hand or finger could be interacting, for example for a certain period of time. Such recording capabilities may save the EMS technician time in data entry or patient charting, and would permit the medical professional to create charting entries and other writings even when the medical professional's hands are dirty, or when the medical professional does not wish to physically touch devices so as to maintain sterility for hands or gloved hands, according to embodiments of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for gesture recognition in an emergency response environment, the method comprising:
   receiving visual information about at least a portion of a body of a caregiver providing care for a patient from at least one sensor, wherein the caregiver is an emergency medical services provider;
   maintaining or creating an emergency encounter record for the patient;
   monitoring the visual information to determine movements of the at least the portion of the body of the caregiver;
   recognizing an occurrence of a gesture based on the movements of the at least the portion of the body of the caregiver;
   determining that the gesture belongs to one gesture type of a plurality of gesture types; and
   recording an entry comprising a physiological parameter of the patient in the emergency encounter record based on the occurrence of the gesture, wherein the entry recorded depends on the determined gesture type, and the entry comprises at least one of a heart rate, a blood pressure, an electrocardiograph (ECG), a temperature, a respiration rate, a blood oxygen level, an end-tidal carbon dioxide level, a pulmonary function, a blood glucose level, and a weight;
   wherein the emergency response environment is an emergency response vehicle.

2. The method of claim 1, wherein the gesture is an artificial gesture.

3. The method of claim 1, wherein the gesture is a natural gesture.

4. The method of claim 1, wherein the at least the portion of the body of the caregiver is a hand of the caregiver.

5. The method of claim 4, wherein the at least the portion of the body of the caregiver comprises one or more digits of the hand of the caregiver.

6. The method of claim 1, wherein the at least the portion of the body of the caregiver is a head of the caregiver.

7. The method of claim 1, wherein the entry comprises a time of the occurrence of the gesture.

8. The method of claim 7, wherein the entry further comprises an identification of the gesture.

9. The method of claim 1, wherein the entry comprises the visual information received corresponding to a time of the occurrence of the gesture.

10. The method of claim 9, the method further comprising receiving audio information, wherein the entry comprises the audio information received corresponding to the time of the occurrence of the gesture.

11. The method of claim 1, further comprising:
    determining an occurrence of a condition other than the gesture; and
    recording the entry in the emergency encounter record only when the occurrence of the condition coincides with the occurrence of the gesture.

12. The method of claim 11, wherein the gesture is a first gesture, and wherein the condition is a second gesture.

13. The method of claim 11, wherein the condition is a position or location of the body of the caregiver with respect to the emergency response environment.

14. The method of claim 1, wherein the at least the portion of the body of the caregiver is a first portion of the body of the caregiver, wherein the gesture is a first gesture, the method further comprising:
  receiving visual information about a second portion of the body of the caregiver from the at least one sensor;
  monitoring the visual information to determine movements of the second portion of the body of the caregiver;
  recognizing an occurrence of a second gesture based on the movements of the second portion of the body of the caregiver; and
  recording the entry in the emergency encounter record based on the occurrence of the first gesture and the occurrence of the second gesture.

15. The method of claim 14, wherein recording the entry comprises recording the entry in the emergency encounter record only when the first and second gestures coincide.

16. The method of claim 14, wherein the first portion of the body of the caregiver is a hand, and wherein the second portion of the body of the caregiver is a head.

17. The method of claim 14, wherein the first portion of the body of the caregiver is a first hand, and wherein the second portion of the body of the caregiver is a second hand.

18. A system for gesture recognition in an emergency response environment, the system comprising:
  at least one sensor configured to receive visual information about at least a portion of a body of a caregiver providing care to a patient, wherein the caregiver is an emergency medical services provider; and
  a control system communicably coupled to the at least one sensor, the control system configured to:
    maintain or create an emergency encounter record for the patient;
    monitor the visual information to determine movements of the at least the portion of the body of the caregiver;
    recognize an occurrence of a gesture based on the movements of the at least the portion of the body of the caregiver;
    determine that the gesture belongs to one gesture type of a plurality of gesture types; and
    record an entry comprising a physiological parameter of the patient in the emergency encounter record based on the occurrence of the gesture, wherein the entry recorded depends on the determined gesture type, and the entry comprises at least one of a heart rate, a blood pressure, an electrocardiograph (ECG), a temperature, a respiration rate, a blood oxygen level, an end-tidal carbon dioxide level, a pulmonary function, a blood glucose level, and a weight;
  wherein the emergency response environment is an emergency response vehicle.

19. The method of claim 1, wherein the emergency encounter record is a patient charting record comprising at least one of a treatment applied to the patient, medication administered to the patient, and vital sign information of the patient.

20. The method of claim 1, wherein the caregiver is an emergency medical services technician.

21. The system of claim 18, wherein the emergency encounter record is a patient charting record comprising at least one of a treatment applied to the patient, medication administered to the patient, and vital sign information of the patient.

22. The system of claim 18, wherein the caregiver is an emergency medical services technician.

23. The method of claim 1, wherein the physiological parameter of the patient comprises at least one of a blood pressure and an ECG waveform.

24. The system of claim 18, wherein the physiological parameter of the patient comprises at least one of a blood pressure and an ECG waveform.

\* \* \* \* \*